United States Patent
Mas Herrero et al.

(10) Patent No.: US 9,822,415 B2
(45) Date of Patent: Nov. 21, 2017

(54) METHOD FOR PREDICTING THE ONSET OF EXTRAPYRAMIDAL SYMPTOMS (EPS) INDUCED BY AN ANTIPSYCHOTIC-BASED TREATMENT

(71) Applicants: UNIVERSITAT DE BARCELONA, Barcelona (ES); HOSPITAL CLÍNIC DE BARCELONA, Barcelona (ES); INSTITUT D'INVESTIGACIONS BIOMÈDIQUES AUGUST PI I SUNYER, Barcelona (ES); CENTRO DE INVESTIGACIÓN BIOMÉDICA EN RED (CIBER), Madrid (ES)

(72) Inventors: Sergi Mas Herrero, Barcelona (ES); Patricia Gassó Astorga, Barcelona (ES); Cristina Malagelada Grau, Barcelona (ES); Miquel Bernardo Arroyo, Barcelona (ES); Amalia Lafuente Flo, Barcelona (ES)

(73) Assignees: UNIVERSITAT DE BARCELONA, Barcelona (ES); HOSPITAL CLINIC DE BARCELONA, Barcelona (ES); INSTITUT D'INVESTIGACIONS BIOMÈDIQUES AUGUST PI I SUNYER, Barcelona (ES); CENTRO DE INVESTIGACIÓN BIOMÉDICA EN RED (CIBER), Madrid (ES)

( * ) Notice: Subject to any disclaimer, the term of this patent is extended or adjusted under 35 U.S.C. 154(b) by 101 days.

(21) Appl. No.: 14/763,292

(22) PCT Filed: Jan. 24, 2014

(86) PCT No.: PCT/EP2014/051369
§ 371 (c)(1),
(2) Date: Jul. 24, 2015

(87) PCT Pub. No.: WO2014/114734
PCT Pub. Date: Jul. 31, 2014

(65) Prior Publication Data
US 2015/0354005 A1  Dec. 10, 2015

(30) Foreign Application Priority Data
Jan. 25, 2013 (EP) .................................. 13382027

(51) Int. Cl.
*C12Q 1/68* (2006.01)

(52) U.S. Cl.
CPC ..... *C12Q 1/6883* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

| WO | WO 2007/144874 | 12/2007 |
| WO | WO 2009/092032 | 7/2009 |
| WO | WO 2011/148379 | 12/2011 |

OTHER PUBLICATIONS

Brook et al Psychopharmacology. 2005. 178: 514-523.*
Edgell et al European Psychiatry. Oct 200. vol. 15, Suppl 2. P02.317, p. 408s.*
Hirschhorn et al. (Genetics in Medicine. vol. 4, No. 2, pp. 45-61, Mar. 2002).*
Lucentini et al the Scientist (2004) vol. 18, p. 20.*
Hattersley et al. The Lancet. 2005. 366: 1315-1323.*
Gagneux (Molecular Phylogenetics and Evolution. 2001. 18: 2-13.*
Halushka et al. Nature. Jul. 1999. 22: 239-247.*
Almoguera et al., "Association of Commen Genetic Variants with Risperidone Adverse Events in a Spanish Schizophrenic Population," Pharmacogenomics J., vol. 13, No. 2 pp. 197-204; DOI: 19.1038/tpj.2011.57 (Epub ahead of print Jan. 3, 2012).
Database GeO, "Illumina: 'Illumina HumanHap550-Duov3 Genotyping BeadChip (HumanHap550-2v3_B)'", NCBI database accession No. GPL6982, Jun. 2008.
Gassó et al., "A Common Variant in DRD3 Gene is Associated with Risperidone-induced Extrapyramidal Symptoms," Pharmacogenomics J., vol. 9 pp. 404-410 (2009).
Greenbaum et al., "Further Evidence for Association of the RGS2 Gene with Antipsychotic-induced Parkinsonism: Protective Role of a Functional Polymorphism in the 3'-untranslated Region," Pharmacogenomics J., vol. 9 pp. 103-110 (2009).
International Search Report corresponding to PCT/EP2014/051369 dated Feb. 26, 2014.
Mas, "Intuitive Pharmacogenetics: Spontaneous Risperidone Dosage is Related to CYP2D6, CYP3A5 and ABCB1 Genotypes," Pharmacogenomics J., vol. 12 pp. 255-259 (2012).

* cited by examiner

*Primary Examiner* — Carla Myers
(74) *Attorney, Agent, or Firm* — Jenkins, Wilson, Taylor & Hunt, P.A.

(57) ABSTRACT

The invention relates to methods for predicting the onset of extrapyramidal symptoms (EPS) induced by an antipsychotic-based treatment as well as methods for providing personalized medicine to patients based on the sequence of several SNPs associated with the onset of EPS. The invention relates as well to kits for carrying out the diagnostic and predictive medicine methods.

9 Claims, No Drawings

SEQUENCE LISTING

<160> NUMBER OF SEQ ID NOS: 4

<210> SEQ ID NO 1
<211> LENGTH: 52
<212> TYPE: DNA
<213> ORGANISM: Homo sapiens
<220> FEATURE:
<221> NAME/KEY: variation
<222> LOCATION: (27)..(27)
<223> OTHER INFORMATION: The K at position 27 can be g or t
<220> FEATURE:
<221> NAME/KEY: variation
<222> LOCATION: (27)..(27)
<223> OTHER INFORMATION: The k at position 27 can be g or t

<400> SEQUENCE: 1
ctggggtttc tcccaggagg tttttgkgct tgcgctggag ggctctggac tc    52

<210> SEQ ID NO 2
<211> LENGTH: 51
<212> TYPE: DNA
<213> ORGANISM: Homo sapiens
<220> FEATURE:
<221> NAME/KEY: variation
<222> LOCATION: (27)..(27)
<223> OTHER INFORMATION: The k at position 27 can be g or t

<400> SEQUENCE: 2
cattctatta tgctcataat aaaaatktac tgaggactct atgccagaaa t    51

<210> SEQ ID NO 3
<211> LENGTH: 52
<212> TYPE: DNA
<213> ORGANISM: Homo sapiens
<220> FEATURE:
<221> NAME/KEY: variation
<222> LOCATION: (27)..(27)
<223> OTHER INFORMATION: The r at position 27 can be a or g

<400> SEQUENCE: 3
aaagcagaag gaaagaaata acaaacrgca gaaatcaata aaatagagta ca    52

<210> SEQ ID NO 4
<211> LENGTH: 52
<212> TYPE: DNA
<213> ORGANISM: Homo sapiens
<220> FEATURE:
<221> NAME/KEY: variation
<222> LOCATION: (27)..(27)
<223> OTHER INFORMATION: The w at position 27 can be a or t

<400> SEQUENCE: 4
gaggcaggag ctgagggact gattccwgtg gttggaaaac tgaggcagcc ac    52

METHOD FOR PREDICTING THE ONSET OF EXTRAPYRAMIDAL SYMPTOMS (EPS) INDUCED BY AN ANTIPSYCHOTIC-BASED TREATMENT

FIELD OF THE INVENTION

The invention relates to methods for predicting the onset of extrapyramidal symptoms (EPS) induced by an antipsychotic-based treatment as well as methods for providing personalized medicine to patients. The invention relates as well to kits for carrying out the diagnostic and predictive medicine methods.

BACKGROUND OF THE INVENTION

Antipsychotic treatment-emergent extrapyramidal symptoms (EPS) are frequent and serious acute adverse reactions of antipsychotic drugs, the signs of which may develop within few days of starting medication. EPS is a complex phenotype that includes several recognized syndromes namely parkinsonism, akathisia, acute dystonia and dyskinesia. While the situation has improved since the pre-clozapine era, the EPS problem has by no means gone away; for example, in CATIE (Comparative Effectiveness of Antipsychotic Medications in Patients with Schizophrenia), a large effectiveness trial, 10.5% of patients stopped their assigned medication for EPS-related reasons.

Even though the exact mechanism underlying EPS is not clear, striatal dopamine D2 receptor (DRD2) blockade is believed to be the principal cause. The essential control of motor activity is assumed by the basal ganglia, whose main constituent is the striatum. In the dorsal striatum, dopamine regulates the motor activity by whether interacting with dopamine D1 receptor (DRD1) or DRD2, resulting in two different projecting pathways ("direct and "indirect" pathways) and most importantly in opposite stimulation of the thalamus. According to this model, dopamine promotes motor activity by increasing the activity of the direct pathway and, concomitantly by inhibiting the indirect pathway.

Several studies have tried to identify potential risk factors for developing EPS, such as younger age, male gender and psychiatric diagnosis, especially mood disorders. Pharmacogenetics markers have been also tested (Zhang and Malhotra, 2011, Expert Opin Drug Metab Toxicol 7:9-37). Although some genetic variant may have significant effects on EPS appearance (Gassó et al., 2009, Pharmacogenomics J 9:404-10; Greenbaum et al., 2009, Pharmacogenomics J 9:103-10) no single factor can predict this phenomenon.

Almoguera et al. [2012, Pharmacogenomics J. doi: 10.1038/tpj.2011.57 (Epub ahead of print Jan. 3, 2012)] describes the association of genetic variants in several genes with adverse effects caused by risperidone in patients with schizophrenia. All analyzed gene variants had been previously described in relation to the ability to predict patient response to risperidone or adverse effects. Almoguera et al. further disclose that ADRB2 gene variants 16Gly, SLC6A4 L/S, SLC6A4 S/S and DRD3 9Gly correlate with the onset of sexual adverse events, somnolence, EPS and weight gain in patients treated with risperidone.

WO 2011/148379 describes genotypes associated with resistance to parkinsonism and other antipsychotic-induced EPS, in particular the rs12678719 SNP in gene ZFPM2 and the rs4606 SNP in gene RGS2.

WO 2007/144874 describes genotypes associated with resistance to EPS induced by antipsychotics, especially the rs2179652, rs1933695, rs2746073, rs4606, rs1819741 and rs1152746 SNPs. Furthermore, this document identifies genotypes associated with a predisposition to the onset or aggravation of EPS. Gene variants associated with EPS are in RGS2 gene.

Xu et al. (2007, J. Clin. Psychiatry, 68:1358-67) describes the identification of the rs3803300 SNP in gene AKT1 and of a haplotype consisting of 5 SNPs in said gene that are associated with the onset of schizophrenia. However, neither the rs3803300 SNP nor the haplotype show any relationship with the onset of EPS.

Thus, there is still a need in the art for a method that allows to predict the onset EPS induced by an antipsychotic-based treatment.

BRIEF DESCRIPTION OF THE INVENTION

The authors of the present invention have identified for the first time a set of single nucleotide polymorphisms (SNPs) which provides a reliable method for the prediction of the onset of extrapyramidal symptoms (EPS) in patients undergoing treatment with antipsychotics. For instance, as shown in example 1 of the application, some allelic combinations of the rs1130214, rs456998, rs7211818 and rs1053639 SNPs predict a high risk of the subject to develop EPS, whereas other allelic combinations predict a low risk of the subject to develop EPS.

Thus, in a first aspect, the invention relates to a method for predicting the onset of extrapyramidal symptoms (EPS) induced by an antipsychotic-based treatment in a subject, comprising
  i) determining the sequence of the rs1130214, rs456998, rs7211818 and rs1053639 single nucleotide polymorphisms (SNPs) in a sample comprising genetic material from said subject, and
  ii) predicting the risk of said subject to develop EPS based on the sequence of said SNPs.

In another aspect, the invention relates to a method for selecting a subject suffering from a disease treatable with antipsychotics to receive a low DRD2 blockade potency antipsychotic-based therapy, comprising
  i) determining the sequence of the rs1130214, rs456998, rs7211818 and rs1053639 SNPs in a sample comprising genetic material from said subject, and
  ii) selecting said subject to receive a low DRD2 blockade potency antipsychotic-based therapy based on the sequence of said SNPs.

In another aspect, the invention relates to a method for selecting a suitable antipsychotic-based therapy to treat a subject suffering from a disease treatable with antipsychotics, comprising
  i) determining the sequence of the rs1130214, rs456998, rs7211818 and rs1053639 SNPs in a sample comprising genetic material from said subject, and
  ii) selecting a suitable antipsychotic-based therapy based on the sequence of said SNPs,
wherein said antipsychotic is selected from the group consisting of a low DRD2 blockade potency antipsychotic-based therapy and any antipsychotic-based therapy.

In another aspect, the invention relates to a kit comprising reagents suitable for determining the sequence of the rs1130214, rs456998, rs7211818 and rs1053639 SNPs, wherein said reagents comprise DNA or RNA probes.

In another aspect, the invention relates to the use of a kit comprising reagents suitable for determining the sequence of the rs1130214, rs456998, rs7211818 and rs1053639 SNPs for predicting the onset of EPS induced by an antipsychotic-based treatment in a subject based on the sequence of the rs1130214, rs456998, rs7211818 and rs1053639 SNPs.

In another aspect, the invention relates to a low DRD2 blockade potency antipsychotic for use in the treatment of a disease treatable with antipsychotics in a subject, wherein said subject has been selected using the method for selecting a subject suffering from a disease treatable with antipsychotics to receive a low DRD2 blockade potency antipsychotic-based therapy.

In another aspect, the invention relates to the use of the rs1130214, rs456998, rs7211818 and rs1053639 SNPs for predicting the onset of EPS induced by an antipsychotic-based treatment in a subject, for selecting a subject suffering from a disease treatable with antipsychotics to receive a low DRD2 blockade potency antipsychotic-based therapy or for selecting a suitable antipsychotic-based therapy to treat a subject suffering from a disease treatable with antipsychotics.

DETAILED DESCRIPTION OF THE INVENTION

The authors of the present invention have identified for the first time a set of single nucleotide polymorphisms (SNPs) which provides a reliable method for the prediction of the onset of extrapyramidal symptoms (EPS) in patients undergoing treatment with antipsychotics.

The inventors performed a study where 241 psychiatric patients receiving an antipsychotic-based therapy were screened for nine SNPs, and studied their contribution to the risk of EPS. They found that the combination of the rs1130214, rs456998, rs7211818 and rs1053639 SNPs was statistically significant. This finding opens the door to new genetic predictors of EPS in the treatment of diseases treatable with antipsychotics, helping the physician in the design of individualized therapy of subjects. Based on these findings, the inventors have developed the methods of the present invention which will be described now in detail.

For the avoidance of doubt, the methods of the invention do not involve diagnosis practiced on the human or animal body. The methods of the invention are preferably conducted on a sample that has previously been removed from the subject. The kits of the invention, described hereunder, may include means for extracting the sample from the subject.

Method for Predicting the Onset of EPS Induced by an Antipsychotic-Based Treatment in a Subject In a first aspect, the invention relates to a method (hereinafter referred to as the "first method of the invention") for predicting the onset of EPS induced by an antipsychotic-based treatment in a subject, comprising
  i) determining the sequence of the rs1130214, rs456998, rs7211818 and rs1053639 single nucleotide polymorphisms (SNPs) in a sample comprising genetic material from said subject, and
  ii) predicting the risk of said subject to develop EPS based on the sequence of said SNPs.

The term "predicting the onset of extrapyramidal symptoms (EPS) induced by an antipsychotic-based treatment", is used herein to refer to the likelihood that a patient will develop EPS as a consequence of a treatment based on antipsychotics. The predictive methods of the present invention can be used clinically to make treatment decisions by choosing the most appropriate treatment modalities for any particular patient. The predictive methods of the present invention are valuable tools in predicting if a patient is likely to develop EPS respond favorably to a treatment regimen, such as an antipsychotic-based treatment. The prediction may include prognostic factors.

As it will be understood by those skilled in the art, the prediction, although preferred to be, need not be correct for 100% of the subjects to be evaluated. The term, however, requires that a statistically significant portion of subjects can be identified as having an increased probability of having a given outcome. Whether a subject is statistically significant can be determined without further ado by the person skilled in the art using various well known statistic evaluation tools, e.g., determination of confidence intervals, p-value determination, cross-validated classification rates and the like etc. Details are found in Dowdy and Wearden, Statistics for Research, John Wiley & Sons, New York 1983. Preferred confidence intervals are at least 50%, at least 60%, at least 70%, at least 80%, at least 90% or at least 95%. The p-values are, preferably, 0.01, 0.005 or lower.

The term "extrapyramidal symptoms" or "EPS" or "extrapyramidal side-effects (EPSE)", as used herein, refers to the various effects on motor control, including acute dystonic reactions, pseudoparkinsonism, akathisia (an inability to sit still), trembling, involuntary repetitive body movements (tardive dyskinesia), suffered as a result of the intake of antipsychotic drugs. EPS are normally rated using the Simpson-Angus Rating Scale. This scale contains 10 items: gait, arm dropping, shoulder shaking, elbow rigidity, wrist rigidity, leg pendulousness, head dropping, glabella tap, tremor, and salivation. Each item is rated between 0 and 4. A total score is obtained by adding the items and dividing by 10. Scores of up to 0.3 are considered within the normal range.

The term "treatment" or "therapy" includes any process, action, application, therapy, or the like, wherein a subject, including a human being, is provided medical aid with the object of improving the subject's condition, directly or indirectly, or slowing the progression of a condition or disorder in the subject, or ameliorating at least one symptom of the disease or disorder under treatment. The term "antipsychotic-based treatment" or "antipsychotic-based therapy", as used herein, refers to any treatment or therapy that comprises at least one antipsychotic.

The term "antipsychotic" or "neuroleptic", as used herein, refers to a psychiatric medication primarily used to manage psychosis (including delusions or hallucinations, as well as disordered thought), and is increasingly being used in the management of non-psychotic disorders. Antipsychotics are designed with the Anatomical Therapeutic Chemical (ATC) code N05A. Antipsychotics are broadly divided into two groups, the typical or first-generation antipsychotics and the atypical or second-generation antipsychotics. The typical antipsychotics are classified according to their chemical structure while the atypical antipsychotics are classified according to their pharmacological properties. These include serotonin-dopamine antagonists (see dopamine antagonist and serotonin antagonist), multi-acting receptor-targeted antipsychotics (MARTA, those targeting several systems), and dopamine partial agonists, which are often categorized as atypicals.

Recently, a new classification system is being used, wherein antipsychotics are divided according to their potency in blocking the dopaminergic receptor D2 (DRD2), i.e. antipsychotics are divided into low, medium and high DRD2 blockade potency antipsychotics. Low DRD2 blockade potency antipsychotics are known in the art to have a lower probability to induce EPS in subjects, where as medium and high DRD2 blockade potency antipsychotics are known in the art to have a higher probability to induce EPS in subjects. Non-limitative examples of low DRD2 blockade potency antipsychotics include clozapine, ziprasidone, quetiapine and olanzapine. Non-limitative examples of medium DRD2 blockade potency antipsychotics include amisulpride, risperidone and zuclopenixol. Non-limitative examples of high DRD2 blockade potency antipsychotics include haloperidol and chlorpromazine (Gardner et al., 2005, Can Med Assoc J 172:1703-11).

The term "subject", as used herein, refers to an individual, such as a human, a nonhuman primate (e.g. chimpanzees and other apes and monkey species); farm animals, such as birds, fish, cattle, sheep, pigs, goats and horses; domestic mammals, such as dogs and cats; laboratory animals including rodents, such as mice, rats and guinea pigs. The term does not denote a particular age or sex. In a particular embodiment of the invention, the subject is a mammal. In a preferred embodiment of the invention, the subject is a human. In a more preferred embodiment of the invention, the subject has been diagnosed with a disease treatable with antipsychotics.

As the person skilled in the art will recognize, an antipsychotic-based treatment is not only aimed at treating a disorder or disease that presents psychosis, and it can be used to treat other kinds of disorders or diseases. Thus, in another particular embodiment of the first method of the invention, the subject suffers a disease treatable with antipsychotics. As used herein, "disease treatable with antipsychotics" refers to any disease or disorder which condition can be improved, which progression can be slowed, or which at least one symptom can be ameliorated under treatment with antipsychotics. Non-limitative examples of diseases treatable with antipsychotics include schizophrenia, schizoaffective disorder, acute psychotic disorder, delusional disorder, schizotypal personality disorder, bipolar disorder, obsessive compulsive disorder, personality disorder, psychotic depression, conduct disorder, cognitive deficits, nausea and vomiting, and Alzheimer disease.

In a first step, the first method of the invention comprises the determination of the sequence of the rs1130214, rs456998, rs7211818 and rs1053639 single nucleotide polymorphisms (SNPs) in a sample comprising genetic material from said subject.

The term "single nucleotide polymorphism" or "SNP", as used herein, refers to a variation in the nucleotide sequence of a nucleic acid that occurs in a single nucleotide (A, C, T or G), wherein each possible sequence is present in a proportion equal to or greater than a 1% of the population. The SNPs are typically named using the accession number in the SNP database (dbSNP) at National Center for Biotechnology Information (NCBI) accessible at http://www.ncbi.nlm.nih.gov/projects/SNP/. In general, SNPs represent one of the most common forms of genetic variations. These polymorphisms appear when a single nucleotide in the genome is altered (such as via substitution, addition or deletion). Each version of the sequence with respect to the polymorphic site is referred to as an allele of the polymorphic site. SNPs tend to be evolutionary stable from generation to generation and, as such, can be used to study specific genetic abnormalities throughout a population. If SNPs occur in the protein coding region, it can lead to the expression of a variant, sometimes defective, form of the protein that may lead to development of a genetic disease. Some SNPs may occur in non-coding regions, but nevertheless, may result in differential or defective splicing, or altered protein expression levels. SNPs can therefore serve as effective indicators of a genetic disease. SNPs can also be used as diagnostic and/or prognostic tools for identifying individuals with a predisposition for a disease or for a fast evolution of the disease, genotyping the individual suffering from the disease, and facilitating drug development based on the insight revealed regarding the role of target proteins in the pathogenesis process. Each version of the sequence with respect to the SNP is referred to as an allele of the SNP.

The term "allele", as used herein, relates to one of two or more forms of a gene, locus or genetic polymorphism. Sometimes, different alleles can result in different traits; however, other times, different alleles will have the same result in the expression of a gene. Most multicellular organisms have two sets of chromosomes, that is, they are diploid. These chromosomes are referred to as homologous chromosomes. Diploid organisms have one copy of each gene (and one allele) on each chromosome. If both alleles are the same, they are homozygotes. If the alleles are different, they are heterozygotes.

The term "sample" or "biological sample", as used herein, refers to biological material isolated from a subject. The biological sample contains any biological material suitable for detecting the desired SNP and can comprise cell and/or non-cell material of the subject. In the present invention, the sample comprises genetic material, e.g., DNA, genomic DNA (gDNA), complementary DNA (cDNA), RNA, heterogeneous nuclear RNA (hnRNA), mRNA, etc., from the subject under study. The sample can be isolated from any suitable tissue or biological fluid such as, for example blood, saliva, plasma, serum, urine, cerebrospinal liquid (CSF), feces, a buccal or buccal-pharyngeal swab, a surgical specimen, and a specimen obtained from a biopsy. Methods for isolating cell and tissue samples are well known to those skilled in the art. In a particular embodiment, the sample is selected from the group consisting of blood, urine, saliva, serum, plasma, a buccal or buccal-pharyngeal swab, hair, a surgical specimen, and a specimen obtained from a biopsy. In preferred embodiment, the sample is selected from blood, hair, urine and saliva.

The terms "determining the sequence of an SNP" or "detecting an SNP" are used indistinctly in the present invention, and refer to the determination of the sequence of a particular SNP in both alleles of the subject under study. The determination of the sequence of the SNP can be performed by means of multiple processes known by the person skilled in the art.

In some embodiments, for example, when the determination of the sequence of the SNPs is carried out in a sample from whole blood, it may be used directly for the detection of said SNPs. In other embodiments, the nucleic acid is extracted from cells which are present in a biological fluid (e.g., whole blood, saliva, synovial fluid, etc.) as an initial step, and, in such cases, the total nucleic acid extracted from said samples would represent the working material suitable for subsequent amplification. Isolating the nucleic acid of the sample can be performed by methods known by the person skilled in the art. Said methods can be found, for example, in Sambrook et al., 2001. "Molecular cloning: a Laboratory Manual", 3rd ed., Cold Spring Harbor Laboratory Press, N.Y., Vol. 1-3. Further, as mentioned above, in some embodiments, generation of nucleic acids for analysis from samples requires nucleic acid amplification. Many amplification methods rely on an enzymatic chain reaction such as, for example, a polymerase chain reaction (PCR), a ligase chain reaction (LCR), or a self-sustained sequence replication, rolling-circle amplification assays, etc.; this list is merely illustrative and in no way limiting. Methods for amplifying nucleic acid are described in Sambrook et al., 2001 (cited at supra).

After isolating, and amplifying (if necessary), the nucleic acid, the sequences of the different SNPs of the invention are detected. Those skilled in the art will readily recognize that the analysis of the nucleotides present in one or several of the SNPs, or polymorphisms, disclosed herein in a patient's nucleic acid can be done by any method or technique capable of determining nucleotides present in a SNP or polymorphism. For instance, one may detect SNPs in the first method of the invention by performing sequencing, mini-sequencing, hybridization, restriction fragment analysis, oligonucleotide ligation assay, allele-specific PCR, or a combination thereof. As such, systems and methods for the detection of SNPs, in general include, but are not limited to, nucleic acid sequencing, hybridization methods and array technology (e.g. technology available from Aclara BioSciences, Affymetrix, Agilent Technologies, Illumina Inc., etc); also techniques based on mobility shift in amplified nucleic acid fragments, Single Stranded Conformational Polymorphism (SSCP), denaturing gradient gel electrophoresis (DGGE), Chemical Mismatch Cleavage (CMC), Restriction Fragment Polymorphisms (RFLPs), and WAVE analysis can be used (Methods Mol. Med. 2004; 108: 173-88), and the like. Of course, this list is merely illustrative and in no way limiting. Those skilled in the art may use any appropriate method to achieve such detection. As it is obvious in the art, the sequence of said SNPs can be determined from either nucleic acid strand or from both strands. In the present invention, the sequences of said SNPs are determined from both strands.

In another particular embodiment, the determination of the sequence of said SNPs is carried out by real-time PCR.

The SNPs used in the present invention are identified below:

rs1130214 is located in the AKT1 gene and corresponds to SEQ ID NO: 1;

```
CTGGGGTTTCTCCCAGGAGGTTTTTG[G/T]GCTTGCGCTGGAGGGCTCT
GGACTC
``` rs456998 is located in the FCHSD1 gene and corresponds to SEQ ID NO: 2;

```
CATTCTATTATGCTCATAATAAAAAT[G/T]TACTGAGGACTCTATGCCA
GAAATT
``` rs7211818 is located in the RPTOR gene and corresponds to SEQ ID NO: 3; and

```
AAAGCAGAAGGAAAGAAATAACAAAC[A/G]GCAGAAATCAATAAAATAG
AGTACA
``` rs1053639 is located in the DDIT4 gene and corresponds to SEQ ID NO: 4.

```
GAGGCAGGAGCTGAGGGACTGATTCC[A/T]GTGGTTGGAAAACTGAGGC
AGCCAC
```

In a second step, the first method of the invention comprises the prediction of the risk of said subject to develop EPS based on the sequence of the rs1130214, rs456998, rs7211818 and rs1053639 SNPs.

In this connection, the invention provides not only some specific SNPs which in combination are significantly associated with the prediction of the onset of EPS induced by an antipsychotic-based treatment in a subject, but also the corresponding allelic combinations for high and low risk to develop EPS of said SNPs, which are mentioned in Tables 1 and 2. Thus, in a particular embodiment, the presence of one allelic combination according to Table 1 is indicative that that there is a high risk of the subject to develop EPS. In another particular embodiment, the presence of one allelic combination according to Table 2 is indicative that there is a low risk of the subject to develop EPS.

TABLE 1

Allelic combinations that predict a high risk to develop EPS

| rs1130214 | rs456998 | rs7211818 | rs1053639 | Predicted Status |
|---|---|---|---|---|
| 1 | 0 | 1 | 0 | EPS |
| 1 | 0 | 1 | 1 | EPS |
| 1 | 2 | 1 | 0 | EPS |
| 1 | 2 | 1 | 2 | EPS |
| 1 | 2 | 0 | 2 | EPS |
| 1 | 2 | 0 | 1 | EPS |
| 1 | 2 | 2 | 1 | EPS |
| 0 | 0 | 0 | 0 | EPS |
| 0 | 2 | 1 | 1 | EPS |
| 0 | 2 | 0 | 0 | EPS |
| 0 | 2 | 2 | 2 | EPS |
| 0 | 1 | 1 | 0 | EPS |
| 0 | 1 | 0 | 1 | EPS |
| 0 | 1 | 2 | 1 | EPS |
| 2 | 0 | 1 | 0 | EPS |
| 2 | 0 | 1 | 2 | EPS |
| 2 | 0 | 1 | 1 | EPS |
| 2 | 0 | 0 | 1 | EPS |
| 2 | 2 | 0 | 2 | EPS |

For each of the SNPs: 0=Homozygosis for allele 1; 1=Heterozygosis for allele 1/allele 2; 2=Homozygosis for allele 2.
rs1130214: —allele 1=G; allele 2=T;
  genotype 0=GG; genotype 1=GT; genotype 2=TT
rs456998: —allele 1=T; allele 2=G;
  genotype 0=TT; genotype 1=GT; genotype 2=GG
rs7211818: —allele 1=A; allele 2=G;
  genotype 0=AA; genotype 1=AG; genotype 2=GG
rs1053639: —allele 1=T; allele 2=A;
  genotype 0=TT; genotype 1=AT; genotype 2=AA

TABLE 2

Allelic combinations that predict a low risk to develop EPS

| rs1130214 | rs456998 | rs7211818 | rs1053639 | Predicted Status |
|---|---|---|---|---|
| 1 | 0 | 0 | 1 | No-EPS |
| 1 | 2 | 1 | 1 | No-EPS |
| 1 | 2 | 0 | 0 | No-EPS |
| 1 | 1 | 1 | 0 | No-EPS |
| 1 | 1 | 1 | 2 | No-EPS |
| 1 | 1 | 1 | 1 | No-EPS |
| 1 | 1 | 0 | 0 | No-EPS |
| 1 | 1 | 0 | 2 | No-EPS |
| 1 | 1 | 0 | 1 | No-EPS |
| 1 | 1 | 2 | 0 | No-EPS |
| 0 | 0 | 1 | 0 | No-EPS |
| 0 | 0 | 1 | 2 | No-EPS |
| 0 | 0 | 1 | 1 | No-EPS |
| 0 | 0 | 0 | 2 | No-EPS |
| 0 | 0 | 0 | 1 | No-EPS |
| 0 | 2 | 1 | 0 | No-EPS |
| 0 | 2 | 0 | 2 | No-EPS |
| 0 | 2 | 0 | 1 | No-EPS |
| 0 | 1 | 1 | 1 | No-EPS |
| 0 | 1 | 0 | 0 | No-EPS |
| 0 | 1 | 0 | 2 | No-EPS |

TABLE 2-continued

Allelic combinations that predict a low risk to develop EPS

| rs1130214 | rs456998 | rs7211818 | rs1053639 | Predicted Status |
|---|---|---|---|---|
| 0 | 1 | 2 | 2 | No-EPS |
| 2 | 2 | 0 | 0 | No-EPS |
| 2 | 2 | 0 | 1 | No-EPS |
| 2 | 2 | 2 | 2 | No-EPS |
| 2 | 1 | 0 | 0 | No-EPS |
| 2 | 1 | 0 | 1 | No-EPS |

For each of the SNPs: 0=Homozygosis for allele 1; 1=Heterozygosis for allele 1/allele 2; 2=Homozygosis for allele 2.
rs1130214: —allele 1=G; allele 2=T;
  genotype 0=GG; genotype 1=GT; genotype 2=TT
rs456998: —allele 1=T; allele 2=G;
  genotype 0=TT; genotype 1=GT; genotype 2=GG
rs7211818: —allele 1=A; allele 2=G;
  genotype 0=AA; genotype 1=AG; genotype 2=GG
rs1053639: —allele 1=T; allele 2=A;
  genotype 0=TT; genotype 1=AT; genotype 2=AA The expression "risk to develop EPS", as used herein, refers to the predisposition, susceptibility or likelihood of a subject being treated with an antipsychotic-based therapy to develop EPS. The risk to develop EPS generally implies that there is a high or a low risk. In this respect, a subject being treated with an antipsychotic-based therapy at high risk to develop EPS is a subject who presents one allelic combination according to Table 1. Thus, a subject at high risk to develop EPS has at least a 50%, or at least a 60%, or at least a 70%, or at least a 80%, or at least a 90%, or at least a 95%, or at least a 97%, or at least a 98%, or at least a 99%, or at least a 100% probability to develop EPS. Similarly, a subject being treated with an antipsychotic-based therapy at low risk to develop EPS is a subject who presents one allelic combination according to Table 2. Thus, a subject at low risk to develop EPS has at least a 0%, or at least a 1%, or at least a 2%, or at least a 3%, or at least a 5%, or at least a 10%, or at least a 20%, or at least a 30%, or at least a 40%, or at least a 49% probability to develop EPS.

In general, the expression "predicting the risk", "prediction of the risk", or similar, relates to the risk that a subject being treated with an antipsychotic-based therapy to develop EPS either high or low. As it will be understood by those skilled in the art, the prediction (or the risk), although preferred to be, need not be correct for 100% of the subjects to be evaluated. The term, however, requires that a statistically significant portion of subjects can be identified as having an increased probability of developing EPS. Whether a subject is statistically significant can be determined without further ado by the person skilled in the art by using various well known statistic evaluation tools, e.g., determination of confidence intervals, p-value determination, Student's t-test, Mann-Whitney test, etc. Details can be found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably 0.1, 0.05, 0.02, 0.01 or lower.

Method for Selecting a Subject Suffering from a Disease Treatable with Antipsychotics to Receive a Low DRD2 Blockade Potency Antipsychotic-Based Therapy The person skilled in the art will realize that the predictive value of the rs1130214, rs456998, rs7211818 and rs1053639 SNPs can be further put in practice to select those patients that are at high risk to develop antipsychotic-induced EPS to receive therapy with a lower probability to induce EPS, i.e. a low DRD2 blockade potency antipsychotic-based therapy. Thus, in another aspect, the invention relates to a method for selecting a subject suffering from a disease treatable with antipsychotics to receive a low DRD2 blockade potency antipsychotic-based therapy (hereinafter referred to as the "second method of the invention"), comprising
  i) determining the sequence of the rs1130214, rs456998, rs7211818 and rs1053639 SNPs in a sample comprising genetic material from said subject, and
  ii) selecting said subject to receive a low DRD2 blockade potency antipsychotic-based therapy based on the sequence of said SNPs.

The terms "subject", "antipsychotics", "disease treatable with antipsychotics", "low DRD2 blockade potency antipsychotic-based therapy", "SNP", "rs1130214", "rs456998", "rs7211818", "rs1053639", and "sample comprising genetic material", and their particulars have been described in detail in the context of the first method of the invention and are used with the same meaning in the context of the second method according to the invention.

In a first step, the second method of the invention comprises determining the sequence of the rs1130214, rs456998, rs7211818 and rs1053639 SNPs in a sample comprising genetic material from said subject. The particulars of determining the sequence of SNPs have been described in detail in the context of the first method of the invention as well as the particulars of the SNPs to be detected and are applied with same meaning in the context of the second method according to the invention.

In a second step, the second method of the invention comprises selecting said subject to receive a low DRD2 blockade potency antipsychotic-based therapy based on the sequence of said SNPs.

In a particular embodiment of the second method of the invention, the subject is selected to receive a low DRD2 blockade potency antipsychotic-based therapy if the presence of one allelic combination according to Table 1 is detected in the sample. In a preferred embodiment, the low DRD2 blockade potency antipsychotic is selected from the group consisting of clozapine, ziprasidone, quetiapine and olanzapine.

In another particular embodiment, the low DRD2 blockade potency antipsychotic-based therapy additionally comprises an adjuvant antiparkinsonian. As used herein, the term "adjuvant" or "adjuvant therapy" refers to any type of treatment of disease treatable with antipsychotics given as additional treatment, usually to decrease the probability of the antipsychotics to induce EPS. The aim of such an adjuvant treatment is to improve the risk of the subject receiving therapy to develop EPS.

As used herein, the term "antiparkinsonian" refers to a type of drug which is intended to treat and relieve the symptoms of Parkinson's disease (PD) or Parkinsonism. Most of these drugs act by either increasing dopamine activity or reducing acetylcholine activity in the central nervous system. Examples of antiparkinsonians include dopaminergic precursors, selective monoamine oxidase b inhibitors, catechol-o-methyl transferase (COMT) inhibitors, dopamine receptor agonists, and anticholinergics. In a preferred embodiment, the antiparkinsonian is an anticholinergic. As used herein, the term "anticholinergic" refers to a class of drugs that inhibit parasympathetic nerve impulses by selectively blocking the binding of the neurotransmitter acetylcholine to its receptor in nerve cells. The nerve fibers of the parasympathetic system are responsible for the involuntary movements of smooth muscles present in the gastrointestinal tract, urinary tract, lungs, etc. Anticholinergics are classified according to the receptors that are affected into antimuscarinic agents, which operate on the muscarinic acetylcholine receptors, and antinicotinic agents, which operate on the nicotinic acetylcholine receptors. Examples of anticholinergics include, but are not limited to, benztropine, ipratropium, oxitropium, tiotropium, glycopyrrolate, oxybutinin, tolterodine, chlorphenamine, diphenhydramin, dimenhydrinate, bupropion, hexamethonium, tubocurarine, dextromethorphan, mecamylamine, and doxacurium.

Method for Selecting a Suitable Antipsychotic-Based Therapy to Treat a Subject Suffering from a Disease Treatable with Antipsychotics The present invention also contemplates the selection of personalized therapies in accordance with the allelic combinations of the rs1130214, rs456998, rs7211818 and rs1053639 SNPs present in the subject to be treated.

Thus, in another aspect, the present invention relates to a method for selecting a suitable antipsychotic-based therapy to treat a subject suffering from a disease treatable with antipsychotics (hereinafter referred to as the "third method of the invention"), comprising
  i) determining the sequence of the rs1130214, rs456998, rs7211818 and rs1053639 SNPs in a sample comprising genetic material from said subject, and
  ii) selecting a suitable antipsychotic-based therapy based on the sequence of said SNPs,
wherein said antipsychotic is selected from the group consisting of a low DRD2 blockade potency antipsychotic-based therapy and any antipsychotic-based therapy.

The terms "subject", "antipsychotic", "antipsychotic-based therapy", "disease treatable with antipsychotics", "low DRD2 blockade potency antipsychotic-based therapy", "SNP", "rs1130214", "rs456998", "rs7211818", "rs1053639", and "sample comprising genetic material", and their particulars have been described in detail in the context of the first method of the invention and are used with the same meaning in the context of the third method according to the invention.

In a first step, the third method of the invention comprises determining the sequence of the rs1130214, rs456998, rs7211818 and rs1053639 SNPs in a sample comprising genetic material from said subject. The particulars of determining the sequence of SNPs have been described in detail in the context of the first method of the invention as well as the particulars of the SNPs to be detected and are applied with same meaning in the context of the third method according to the invention.

In a second step, the third method of the invention comprises selecting a suitable antipsychotic-based therapy based on the sequence of said SNPs, wherein said antipsychotic is selected from the group consisting of a low DRD2 blockade potency antipsychotic-based therapy and any antipsychotic-based therapy.

In a particular embodiment, the presence of one allelic combination according to Table 1 is indicative that said subject is selected to receive a low DRD2 blockade potency antipsychotic-based therapy, and the presence of one allelic combination according to Table 2 is indicative that the subject is selected to receive any antipsychotic-based therapy.

In a preferred embodiment, the low DRD2 blockade potency antipsychotic is selected from the group consisting of clozapine, ziprasidone, quetiapine and olanzapine.

In another preferred embodiment, the low DRD2 blockade potency antipsychotic-based therapy additionally comprises an adjuvant antiparkinsonian. In a more preferred embodiment, the adjuvant antiparkinsonian is an anticholinergic. The terms "adjuvant" and "antiparkinsonian" and their particulars have been described in detail in the context of the second method of the invention and are used with the same meaning in the context of the third method according to the invention.

The term "any antipsychotic-based therapy", as used herein, refers to a therapy based on an antipsychotic indistinctly selected from the group consisting of a low DRD2 blockade potency antipsychotic, a medium DRD2 blockade potency antipsychotic, and a high DRD2 blockade potency antipsychotic. Thus, in a preferred embodiment, the any antipsychotic-based therapy is selected from the group consisting of a low DRD2 blockade potency antipsychotic, a medium DRD2 blockade potency antipsychotic and a high DRD2 blockade potency antipsychotic. In a more preferred embodiment, the low DRD2 blockade potency antipsychotic is selected from the group consisting of clozapine, ziprasidone, quetiapine and olanzapine. In another more preferred embodiment, the medium DRD2 blockade potency antipsychotic is selected from the group consisting of amisulpride, risperidone and zuclopenixol. In another more preferred embodiment, the high DRD2 blockade potency antipsychotic is selected from the group consisting of haloperidol and chlorpromazine.

Kits of the Invention

The present invention also contemplates the preparation of kits for use in accordance with the present invention.

Thus, in another aspect, the present invention relates to a kit (hereinafter referred to as the "kit of the invention"), comprising reagents suitable for determining the sequence of the rs1130214, rs456998, rs7211818 and rs1053639 SNPs, wherein the reagents of the kit comprise DNA or RNA probes.

Suitable kits include various reagents for use in accordance with the present invention in suitable containers and packaging materials, including tubes, vials, and shrink-wrapped and blow-molded packages. Additionally, the kits of the invention can contain instructions for the simultaneous, sequential or separate use of the different components which are in the kit. Said instructions can be in the form of printed material or in the form of an electronic support capable of storing instructions such that they can be read by a subject, such as electronic storage media (magnetic disks, tapes and the like), optical media (CD-ROM, DVD) and the like. Additionally or alternatively, the media can contain Internet addresses that provide said instructions.

Materials suitable for inclusion in an exemplary kit in accordance with the present invention comprise one or more of the following: gene specific PCR primer pairs (oligonucleotides) that anneal to DNA or cDNA sequence domains that flank the rs1130214, rs456998, rs7211818 and rs1053639 SNPs; reagents capable of amplifying a specific sequence domain in either genomic DNA or cDNA without the requirement of performing PCR; reagents required to discriminate between the various possible alleles in the sequence domains amplified by PCR or non-PCR amplification (e.g., restriction endonucleases, oligonucleotide that anneal preferentially to one allele of the polymorphism, including those modified to contain enzymes or fluorescent chemical groups that amplify the signal from the oligonucleotide and make discrimination of alleles more robust); or reagents required to physically separate products derived from the various alleles (e.g. agarose or polyacrylamide and a buffer to be used in electrophoresis, HPLC columns, SSCP gels, formamide gels or a matrix support for MALDI-TOF).

Specifically contemplated are kits comprising two or more allele-specific oligonucleotides or oligonucleotide pairs, wherein each of the allele-specific oligonucleotide or oligonucleotide pair is directed to one of the rs1130214, rs456998, rs7211818 and rs1053639 SNPs. It will be appreciated that in this context the term "directed to" means an oligonucleotide or oligonucleotide pair capable of identifying the allele present at the SNP. By way of illustration, the present invention contemplates a kit comprising a probe set, comprising a plurality of oligonucleotide probes that interrogate the rs1130214, rs456998, rs7211818 and rs1053639 SNPs, wherein said oligonucleotide probes make up at least 10%, at least 20%, at least 30%, at least 40%, at least 50%, at least 60%, at least 70%, at least 80% or at least 90% of the oligonucleotide probes in the probe set.

In a particular embodiment, the kit includes a set of at least four oligonucleotide probes, each oligonucleotide probe specific to one allele of the rs1130214, rs456998, rs7211818 and rs1053639 SNPs, wherein said oligonucleotide probes make up at least 10%, at least 20%, at least 30%, at least 40%, at least 50%, at least 60%, at least 70%, at least 80% or at least 90% of the oligonucleotide probes in the probe set. In a preferred embodiment, the kit includes a set of four oligonucleotide probes, each specific to one allele of the rs1130214, rs456998, rs7211818 and rs1053639 SNPs.

In a particular embodiment, the kit includes a set of at least four oligonucleotide pair probes, each oligonucleotide pair probe specific to one allele of the rs1130214, rs456998, rs7211818 and rs1053639 SNPs, wherein said oligonucleotide pair probes make up at least 10%, at least 20%, at least 30%, at least 40%, at least 50%, at least 60%, at least 70%, at least 80% or at least 90% of the oligonucleotide probes in the probe set. In a preferred embodiment, the kit includes a set of four oligonucleotide pair probes, each specific to one allele of the rs1130214, rs456998, rs7211818 and rs1053639 SNPs.

In another aspect, the present invention relates to the use of a kit according the invention for predicting the onset of EPS induced by an antipsychotic-based treatment in a subject based on the sequence of the rs1130214, rs456998, rs7211818 and rs1053639 SNPs. The particulars of the kit according to the invention have been described in detail in the context of the kit of the invention and are applied with same meaning in the context of the uses of said kit.

Personalized Therapies of the Invention

The second method of the invention defined above also allows providing personalized therapies to patients suffering a disease treatable with antipsychotics. In particular, patients which are considered as having a high risk to develop EPS will most likely benefit from an antipsychotic-based therapy known to have a lower probability to induce EPS. Conversely, patients showing low risk to develop EPS may do with any antipsychotic-based therapy.

Thus, in another aspect, the invention relates to a low DRD2 blockade potency antipsychotic for use in the treatment of a disease treatable with antipsychotics in a subject (hereinafter referred to as "personalised therapy of the invention"), wherein said subject is selected according to the second method of the invention.

The particulars of the second method of the invention have been described in detail in the context of said second method of the invention, and are applied with same meaning in the context of the personalised therapy according to the invention.

The terms "subject", "antipsychotic", "treatment", "disease treatable with antipsychotics", and "low DRD2 blockade potency antipsychotic" and their particulars have been described in detail in the context of the first method of the invention and are used with the same meaning in the context of the personalised therapy according to the invention.

In a particular embodiment, the low DRD2 blockade potency antipsychotic is selected from the group consisting of clozapine, ziprasidone, quetiapine and olanzapine.

In another particular embodiment, the low DRD2 blockade potency antipsychotic-based therapy additionally comprises an adjuvant antiparkinsonian. In a more preferred embodiment, the adjuvant antiparkinsonian is an anticholinergic. The terms "adjuvant" and "antiparkinsonian" and their particulars have been described in detail in the context of the second method of the invention and are used with the same meaning in the context of the personalised therapy of the invention.

Uses of the Invention

In another aspect, the invention relates to the use of the rs1130214, rs456998, rs7211818 and rs1053639 SNPs for predicting the onset of EPS induced by an antipsychotic-based treatment in a subject (hereinafter referred to as the "first use of the invention").

In a particular embodiment of the first use of the invention, the presence of one allelic combination according to Table 1 is indicative that that there is a high risk of the subject to develop EPS.

In another particular embodiment of the first use of the invention, the presence of one allelic combination according to Table 2 is indicative that there is a low risk of the subject to develop EPS.

In another aspect, the invention relates to the use of the rs1130214, rs456998, rs7211818 and rs1053639 SNPs for selecting a subject suffering from a disease treatable with antipsychotics to receive a low DRD2 blockade potency antipsychotic-based therapy (hereinafter referred to as the "second use of the invention").

In a particular embodiment of the second use of the invention, the subject is selected to receive a low DRD2 blockade potency antipsychotic-based therapy if the presence of one allelic combination according to Table 1 is detected in the sample.

In another aspect, the invention relates to the use of the rs1130214, rs456998, rs7211818 and rs1053639 SNPs for selecting a suitable antipsychotic-based therapy to treat a subject suffering from a disease treatable with antipsychotics (hereinafter referred to as the "third use of the invention").

In a particular embodiment of the third use of the invention, the presence of one allelic combination according to Table 1 is indicative that said subject is selected to receive a low DRD2 blockade potency antipsychotic-based therapy.

In another particular embodiment of the first use of the invention, the presence of one allelic combination according to Table 2 is indicative that the subject is selected to receive any antipsychotic-based therapy.

The terms and particulars of the first, second and third methods of the invention have been described in detail in the context of the methods of the invention and are used with the same meaning in the context of the uses according to the invention.

The invention is detailed below by means of the following examples which are merely illustrative and by no means limiting for the scope of the invention.

Examples

Materials and Methods

Subjects

Sample size calculations assuming a 5% level of significance, 80% power and a EPS risk (odds ratio) of 2 associated with carrying the studied alleles (allelic frequencies>0.1). Calculations were performed with Quanto1.2 software (http://hydra.usc.edu/gxe).

A cohort of 321 psychiatric inpatients receiving antipsychotic therapy was recruited consecutively in the Psychiatry Service of the Hospital Clínic (Barcelona, Spain) over a period of three years (2002-2004). 241 subjects of this cohort participated in the pharmacogenetic study of EPS presented here. Subjects were diagnosed according to DSM-IV criteria: 184 subjects were diagnosed with schizophrenia (n=125) and related disorders (n=22 schizoaffective disorder; n=27 acute psychotic disorder; n=9 delusional paranoid disorder; n=1 schizotypical disorder); 40 were diagnosed as having bipolar disorders; and 17 had other diagnoses (including personality disorder, psychotic depression, behavior disorder, mild cognitive impairment and obsessive-compulsive disorder). Acute EPS induced by antipsychotic medication was evaluated using the Simpson-Angus Scale48. 69 patients presenting EPS (Simpson-Angus>3) during the hospitalization period and/or a history of movement disorders were considered as cases. 172 patients without EPS (Simpson-Angus≤3) at the time of the study or previously were taken as controls. A full description of these populations can be found in previous studies (Gassó et al., 2009, cited supra; Mas et al., 2012, Pharmacogenomics J 12:255-9). Written informed consent and whole blood samples were obtained from each subject. The study was approved by the Ethics Committee of the Hospital Clínic.

To obtain independent data sets for prediction construction and predictor evaluation, the data set was split into a training population, and a validation population. To this end, division was made according to antipsychotic treatment: a cohort of patients treated with risperidone (n=114, 39 cases and 75 controls) (cohort 1) was used to train the data and test the best predictor; a second cohort (n=127, 30 cases and 97 controls) (cohort 2) with the rest of patients treated with other antipsychotic different than risperidone (haloperidol n=27; clozapine n=24; amisulpride n=3; olanzapine n=34; zuclopentixol n=6; ziprasidone n=10; quetiapine n=22) was used to validate the predictor. As a final step the authors of the present invention tested the predictor in the whole cohort, referred as cohort 3 (n=241) (cohort1+cohort3).

SNPs Selection and Genotyping

SNPs of the different nine genes participating in the regulation of mTOR pathway genes were selected according to the following strategy: first, a literature research was conducted using several databases (PubMed, Ensembl, Genetic Association Database, SZGene, PDGene, AlzGene, MSGene) to find SNPs in those genes which were associated with mental disorders; second, if no SNP could be found, SNPs associated with other diseases were looked for since this association could means a functional change in the protein; third, if for some gene no SNP could be selected from the previous steps, a search was performed using PupaSuit database to detected SNPs with predicted functionality; finally the type (coding synonymous, coding non-synonymous, intron, mRNA utr) and frequency of the SNP were checked with the NCBI's SNP database (http://www.ncbi.nlm.nih.gov/snp). A frequency lower than 10% lead to exclusion. The selected SNPs are specified in Table 3.

Polymorphisms (Table 3) were detected with real-time PCR by TaqMan allelic discrimination pre-designed assays (TaqMan-SNP genotyping assays; probe C_32127211_20 to detect rs7874234, probe C_3282533_10 to detect rs13335638, probe C_11647371_10 to detect rs2024627, probe C_26352825_10 to detect rs1130214, probe C_31167105_10 to detect rs456998, probe C_8701299_10 to detect rs1801582, probe C_2747617_30 to detect rs3737597, probe C_1971465_10 to detect rs7211818, probe C_9596692_10 to detect rs1053639), from Applied Biosystems according to the manufacturer's guidelines (Applied Biosystems, Foster City, Calif.).

TABLE 3

List of selected genes of mTOR pathway and SNPs with corresponding alleles and functionality information, together with the p-value for the Hardy-Weinberg equilibrium, the allelic frequencies in cases (EPS) and controls (No-EPS), and the p-value of the allelic association analysis adjusted by sex and age in Cohort 1.

| Gene | SNP | Allele[1] | Functionality related to | H-W[2] | EPS[3] | No-EPS[4] | p-value[5] |
|---|---|---|---|---|---|---|---|
| TSC1 | rs7874234 | C/<u>T</u> | Increased transcription | 0.307 | 0.26 | 0.23 | 0.605 |
| TSC2 | rs13335638 | <u>C</u>/T | High conservative region | 0.301 | 0.25 | 0.23 | 0.595 |
| mTOR | rs2024627 | T/<u>C</u> | High conservative region | 0.326 | 0.26 | 0.24 | 0.825 |
| AKT1 | rs1130214 | G/<u>T</u> | Increased transcription | 0.541 | 0.33 | 0.35 | 0.859 |
| FCHSD1 | rs456998 | <u>G</u>/T | Cisplatin-induced cytotoxicity | 0.357 | 0.45 | 0.49 | 0.797 |
| PARK2 | rs1801582 | C/<u>G</u> | Sporadic Parkinson's disease | 0.587 | 0.20 | 0.22 | 0.664 |
| DISC1 | rs3737597 | C/<u>T</u> | Schizophrenia | 1.0 | 0.04 | 0.02 | 0.422 |
| Raptor | rs7211818 | A/<u>G</u> | Bladder cancer risk | 0.601 | 0.28 | 0.19 | 0.091 |
| DDIT4 | rs1053639 | <u>A</u>/T | Regulatory region | 0.708 | 0.44 | 0.42 | 0.812 |

[1]Underlined the associated allele.
[2]p-value for the Hardy-Weinberg equilibrium in cases and controls.
[3]Allele frequency in cases (EPS).
[4]Allelic frequency in controls (No-EPS).
[5]After bonferroni correction, significant pvalue <0.005.

Statistics

To estimate the independent contribution of each SNP to EPS risk, genotype frequencies were assessed by means of multivariate methods based on logistic regression analysis, using the SNPassoc R package. Also, the SNP data were checked for any departure from Hardy-Weinberg equilibrium in both populations, cases and controls. Then gene-gene interactions were analyzed by multifactor dimensionality reduction (MDR), as described elsewhere, using the MDR 2.0 software available at the open-source MDR project (www.epistasis.org/software.html). First, using Cohort 1 all possible SNP combinations were constructed by testing all possible two- to four-loci interactions using 10-fold cross-validation in an exhaustive search (the sample was split in ten parts, using nine parts to train the data, and one part to test. The process was repeated ten times, using each time a different part to test). As outcome parameters, the authors of the present invention considered cross-validation consistency (measures the consistency of the identification of the variations selected on the basis of the best model applied to computation during the 10-fold cross-validation), testing balanced accuracy (measures the degree to which interaction accurately predicts case-control status and is the mean of the testing performed in the 10-fold cross-validation (label 1 indicates good prediction by the model; label 0.5 indicates that the model was no better than chance in selecting cases from controls) and statistical significance (the p-value of the best model was corrected for multiple testing by 10,000 permutations with the MDR Permutation Testing Module 1.0). Second, a new multilocus attribute with the best model obtained was created. This is the model with the best outcome parameters described above. The new attribute was constructed and re-analyzed in order to calculate the statistics in the Cohort 1 whole dataset, obtaining the odds-ratio and its confidence interval, p-value, sensitivity (TP/TP+FN, measures the ability to correctly predict EPS cases), specificity (TN/TN+FP, measures the ability to correctly reject no-EPS controls), accuracy (TP+TN/TP+TN+FP+FN, measures the ability to correctly predict EPS and no-EPS patients) and precision (TP/TP+FP, measure the truly predicted EPS cases). Thirdly, the constructed attribute was validated in Cohort 2, and Cohort 3 obtaining the same statistics as in cohort 1 whole dataset; odds-ratio and its confidence interval, p-value, sensitivity, specificity, accuracy and precision.

Results

None of the nine SNPs studied alone contributes significantly to the risk of EPS when were tested in Cohort 1. Table 3 summarizes the allelic frequencies in cases and controls, the logistic regression analysis adjusted by sex and age, and also the p-value for the Hardy-Weinberg equilibrium.

The results of the exhaustive MDR analysis are given in Table 4. A four-way model including rs1130214 (AKT1), rs456998 (FCHSD1), rs7211818 (Raptor) and rs1053639 (DDIT4) variants had the best overall performances (testing accuracy 0.660) and a cross-validation consistency of 10/10 (permutation testing p<0.0001).

TABLE 4

Results of the multifactor dimension reduction analysis used in Cohort 1 showing the best model of all possible one- to four-loci interactions and their outcome parameters, including training and testing accuracy, 10-fold cross-validation consistency and model p-value.

| Model | Training Accuracy[1] | Testing Accuracy[2] | CVC[3] | p-value[4] |
|---|---|---|---|---|
| rs456998 | 0.602 | 0.514 | 5/10 | >0.05 |
| rs1130214 rs456998 | 0.656 | 0.525 | 6/10 | >0.05 |
| rs1130214 rs456998 rs1053639 | 0.725 | 0.550 | 6/10 | >0.05 |

TABLE 4-continued

Results of the multifactor dimension reduction analysis used in Cohort 1 showing the best model of all possible one- to four-loci interactions and their outcome parameters, including training and testing accuracy, 10-fold cross-validation consistency and model p-value.

| Model | Training Accuracy[1] | Testing Accuracy[2] | CVC[3] | p-value[4] |
|---|---|---|---|---|
| rs1130214 rs456998 rs7211818 rs1053639 | 0.837 | 0.660 | 10/10 | <0.0001 |

[1]Accuracy in the 10-fold training dataset.
[2]Accuracy in the 10-fold testing dataset.
[3]10-fold cross-validation consistency.
[4]p-value of the best model corrected by 10,000 permutations.

A multilocus attribute with the four SNPs identified was constructed and tested in the whole dataset of cohort 1. Two types of attributes were identified, i.e. predisposing (Table 1) and non-predisposing (Table 2). Carriers of the predisposing attribute (78.9% of cases vs. 11.8% of controls) were 27 times more likely to suffer EPS than those without the attribute (OR 27.91; 95% CI 9.81-79.39; p-value<0.0001). The constructed predisposing genetic attribute correctly predicts 97 of 114 patients (85.1% accuracy), including 30 of 39 cases with EPS (76.9% sensitivity), and 67 of 75 controls without EPS (89.3% specificity). The attribute predicted 38 cases, 30 true positives and 8 false positives (78.9% precision) (Table 5).

TABLE 5

Whole dataset statistics after the application of predictors in Cohort 1, Cohort 2 and Cohort 3.

| | Cohort 1 | Cohort 2 | Cohort 3 |
|---|---|---|---|
| Accuracy | 0.85 | 0.80 | 0.84 |
| Sensitivity | 0.76 | 0.70 | 0.85 |
| Specificity | 0.89 | 0.90 | 0.83 |
| Precision | 0.78 | 0.70 | 0.67 |

As testing a predictor in the same population used to training the data is overoptimistic, the authors of the present invention used cohort 2 to independently validate the constructed attribute. When the attribute was tested in the whole data set of cohort 2, accuracy decreased to 73.23%. As cohort 2 was formed by patients treated with different types of antipsychotic (in contraposition to cohort 1, which includes only patients in treatment with risperidone), a new variable was included in the model to account for this variability. Antipsychotics were categorized according to their potency to blockade DRD2. When this new variable (antipsychotic potency) was added to the predisposing genetic attribute identified in cohort 1, accuracy in cohort 2 increased up to 80.36% (109 patients correctly predicted of 127) (Table 5); carriers of the new predisposing attribute (70.0% of cases vs. 9.27% of controls) were 22 times more likely to suffer EPS than those without the attribute (OR 22.81; 95% CI 8.06-64.50; p-value<0.0001).

The new predictor that includes the four SNPs (identified in cohort 1) and the antipsychotic potency (included in the analysis in cohort 2) was validated in cohort 3 (cohort 1 plus cohort 3). Carriers of the predisposing attribute (85.5% of cases vs. 16.3% of controls) were 30 times more likely to suffer EPS than those without the attribute (OR 30.24; 95% CI 13.86-66.39; p-value<0.0001). As could be observed in Table 3 similar values of accuracy (203 cases correctly predicted of 241), sensitivity (59 of 69 cases with EPS correctly predicted) and specificity (149 controls without EPS of 172 correctly predicted) were obtained with cohort 3. Precision was diminished in cohort 3 respect cohort 1 (from 78.95% to 67.82%).

The invention claimed is:

1. A method for identifying and treating a human subject at increased risk of developing extrapyramidal symptoms (EPS) in response to anti-psychotic medication, the method comprising:

(a) obtaining a nucleic acid sample from a human subject;

(b) performing a nucleic acid based detection assay on the nucleic acid sample to detect the presence of a G and/or a T allele at single nucleotide polymorphism (SNP) rs1130214, a G and/or a T allele at SNP rs456998, an A and/or a G allele at SNP rs7211818, and an A and/or a T allele at SNP rs1053639;

(c) generating a haplotype for the human subject consisting of alleles present at each of SNPs rs1130214, rs456998, rs7211818, and rs1053639;

(d) identifying the human subject as having an increased risk of developing EPS if the human subject has a haplotype selected from the group consisting of Haplotypes A-S, wherein Haplotypes A-S are defined as follows:

Haplotype A is G/T at rs11302141; T/T at rs456998; A/G at rs7211818; T/T at rs1053639;

Haplotype B is G/T at rs11302141; T/T at rs456998; A/G at rs7211818; A/T at rs1053639;

Haplotype C is G/T at rs11302141; G/G at rs456998; A/G at rs7211818; T/T at rs1053639;
Haplotype D is G/T at rs11302141; G/G at rs456998; A/G at rs7211818; A/A at rs1053639;
Haplotype E is G/T at rs11302141; G/G at rs456998; A/A at rs7211818; A/A at rs1053639;
Haplotype F is G/T at rs11302141; G/G at rs456998; A/A at rs7211818; A/T at rs1053639;
Haplotype G is G/T at rs11302141; G/G at rs456998; G/G at rs7211818; A/T at rs1053639;
Haplotype H is G/G at rs11302141; T/T at rs456998; A/A at rs7211818; T/T at rs1053639;
Haplotype I is G/G at rs11302141; G/G at rs456998; A/G at rs7211818; A/T at rs1053639;
Haplotype J is G/G at rs11302141; G/G at rs456998; A/A at rs7211818; T/T at rs1053639;
Haplotype K is G/G at rs11302141; G/G at rs456998; G/G at rs7211818; A/A at rs1053639;
Haplotype L is G/G at rs11302141; G/T at rs456998; A/G at rs7211818; T/T at rs1053639;
Haplotype M is G/G at rs11302141; G/T at rs456998; A/A at rs7211818; A/T at rs1053639;
Haplotype N is G/G at rs11302141; G/T at rs456998; G/G at rs7211818; A/T at rs1053639;
Haplotype O is T/T at rs11302141; T/T at rs456998; A/G at rs7211818; T/T at rs1053639;
Haplotype P is T/T at rs11302141; T/T at rs456998; A/G at rs7211818; A/A at rs1053639;
Haplotype Q is T/T at rs11302141; T/T at rs456998; A/G at rs7211818; A/T at rs1053639;
Haplotype R is T/T at rs11302141; T/T at rs456998; A/A at rs7211818; A/T at rs1053639; and
Haplotype S is T/T at rs11302141; G/G at rs456998; A/A at rs7211818; A/A at rs1053639; and (e) administering a low blockade potency dopaminergic receptor D2 (DRD2) anti-psychotic therapy to the human subject identified in step (d) as having one of Haplotypes A-S to thereby treat the human subject.

2. The method of claim 1, further comprising administering an adjuvant antiparkinsonian to the human subject.

3. The method of claim 1, wherein the adjuvant antiparkinsonian comprises an anticholinergic.

4. The method of claim 1, wherein the nucleic acid based detection assay employs DNA or RNA probes suitable for determining the sequence of the rs1130214, rs456998, rs7211818 and rs1053639 SNPs.

5. A method for treating a human subject in need of treatment with an anti-psychotic medication comprising administering a low potency blockade domaminergic receptor D2 (DRD2) antipsychotic-based therapy to the human subject, wherein a DNA sample from the human subject has previously been tested to detect the presence of a G and/or a T allele at single nucleotide polymorphism (SNP) rs1130214, a G and/or a T allele at SNP rs456998, an A and/or a G allele at SNP rs7211818, and an A and/or a T allele at SNP rs1053639, and further wherein the human subject has a haplotype selected from the group consisting of haplotypes A-S, wherein haplotypes A-S are defined as follows:

Haplotype A is G/T at rs11302141; T/T at rs456998; A/G at rs7211818; T/T at rs1053639;
Haplotype B is G/T at rs11302141; T/T at rs456998; A/G at rs7211818; A/T at rs1053639;
Haplotype C is G/T at rs11302141; G/G at rs456998; A/G at rs7211818; T/T at rs1053639;
Haplotype D is G/T at rs11302141; G/G at rs456998; A/G at rs7211818; A/A at rs1053639;
Haplotype E is G/T at rs11302141; G/G at rs456998; A/A at rs7211818; A/A at rs1053639;
Haplotype F is G/T at rs11302141; G/G at rs456998; A/A at rs7211818; A/T at rs1053639;
Haplotype G is G/T at rs11302141; G/G at rs456998; G/G at rs7211818; A/T at rs1053639;
Haplotype H is G/G at rs11302141; T/T at rs456998; A/A at rs7211818; T/T at rs1053639;
Haplotype I is G/G at rs11302141; G/G at rs456998; A/G at rs7211818; A/T at rs1053639;
Haplotype J is G/G at rs11302141; G/G at rs456998; A/A at rs7211818; T/T at rs1053639;
Haplotype K is G/G at rs11302141; G/G at rs456998; G/G at rs7211818; A/A at rs1053639;
Haplotype L is G/G at rs11302141; G/T at rs456998; A/G at rs7211818; T/T at rs1053639;
Haplotype M is G/G at rs11302141; G/T at rs456998; A/A at rs7211818; A/T at rs1053639;
Haplotype N is G/G at rs11302141; G/T at rs456998; G/G at rs7211818; A/T at rs1053639;
Haplotype 0 is T/T at rs11302141; T/T at rs456998; A/G at rs7211818; T/T at rs1053639;
Haplotype P is T/T at rs11302141; T/T at rs456998; A/G at rs7211818; A/A at rs1053639;
Haplotype Q is T/T at rs11302141; T/T at rs456998; A/G at rs7211818; A/T at rs1053639;
Haplotype R is T/T at rs11302141; T/T at rs456998; A/A at rs7211818; A/T at rs1053639; and
Haplotype S is T/T at rs11302141; G/G at rs456998; A/A at rs7211818; A/A at rs1053639.

6. The method of claim 5, further comprising administering an adjuvant antiparkinsonian to the human subject.

7. The method of claim 5, wherein the adjuvant antiparkinsonian comprises an anticholinergic.

8. The method of claim 5, wherein the DNA sample from the human subject has previously been tested to detect the presence of a G and/or a T allele at single nucleotide polymorphism (SNP) rs1130214, a G and/or a T allele at SNP rs456998, an A and/or a G allele at SNP rs7211818, and an A and/or a T allele at SNP rs1053639 using a nucleic acid based detection assay that employs DNA or RNA probes suitable for determining the sequence of the rs1130214, rs456998, rs7211818 and rs1053639 SNPs.

9. The method of claim 5, wherein the disease treatable with antipsychotics is selected from the group consisting of schizophrenia, schizoaffective disorder, acute psychotic disorder, delusional disorder, schizotypal personality disorder, bipolar disorder, obsessive compulsive disorder, personality disorder, psychotic depression, conduct disorder, cognitive deficits, nausea and vomiting, and Alzheimer disease.

* * * * *